United States Patent
Shankar et al.

(10) Patent No.: US 10,941,096 B2
(45) Date of Patent: Mar. 9, 2021

(54) **PROCESS FOR THR PREPARATION OF NATURAL CRYSTALLIZED THYMOL FROM *MONARDA CITRIODORA* (JAMMU MONARDA) OIL**

(71) Applicant: Council of Scientific and Industrial Research, New Delhi (IN)

(72) Inventors: Ravi Shankar, Jammu Kashmir (IN); Suresh Chandra, Jammu Kashmir (IN); Siya Ram Meena, Jammu Kashmir (IN); Mahendra Kumar Verma, Jammu Kashmir (IN); Kushal Bindu, Jammu Kashmir (IN); Bhavna Vij, Jammu Kashmir (IN); Divya Dheer, Jammu Kashmir (IN); Jyoti, Jammu Kashmir (IN); Ram Asrey Vishwakarma, Jammu Kashmir (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/959,615

(22) PCT Filed: Jan. 3, 2019

(86) PCT No.: PCT/IN2019/050003
§ 371 (c)(1),
(2) Date: Jul. 1, 2020

(87) PCT Pub. No.: WO2019/135255
PCT Pub. Date: Jul. 11, 2019

(65) Prior Publication Data
US 2020/0385326 A1    Dec. 10, 2020

(30) Foreign Application Priority Data
Jan. 3, 2018 (IN) ............................ 201811000289

(51) Int. Cl.
C07C 37/84    (2006.01)

(52) U.S. Cl.
CPC .......... *C07C 37/84* (2013.01); *C07B 2200/13* (2013.01)

(58) Field of Classification Search
CPC ...................................................... C07C 37/84
See application file for complete search history.

(56) References Cited

U.S. PATENT DOCUMENTS 9,745,242 B1    8/2017    Greaves et al.

OTHER PUBLICATIONS

European Patent Office, International Search Report and Written Opinion in International Application No. PCT/IN2019/050003, dated Apr. 11, 2019.
David Villanueva Bermejo et al., "Extraction of thymol from different varieties of thyme plants using green solvents", Journal of the Science of Food and Agriculture, 95(14):2901-2907, Dec. 30, 2014.

*Primary Examiner* — Sikarl A Witherspoon
(74) *Attorney, Agent, or Firm* — Fish & Richardson P.C.

(57) ABSTRACT

The present invention provides an efficient process for the isolation of natural crystallized thymol product derived from crude natural *Monarda citriodora* (Jammu Monarda) oil useful for incorporation into foods and beverages in amounts due to strong antimicrobial, antibacterial, antioxidant properties as well as for use as a preservative. The recovery of crystallized thymol product obtained is more than 72% from Hexane-Jammu Monarda oil in a ratio 1:1 under specific conditions. A method for preparing natural thymol in crystal form involves providing crude Jammu Monarda oil in a Flask and gradually reducing the temperature of the flask containing Monarda oil:Hexane in a step-wise manner, thereby producing highly pure crystals ($\geq 95.5\%$) within 48 h. The methods disclosed herein are suitable for pharmaceutical GMP.

5 Claims, 3 Drawing Sheets

PROCESS FOR THE PREPARATION OF NATURAL CRYSTALLIZED THYMOL FROM *MONARDA CITRIODORA* (JAMMU MONARDA) OIL

FIELD OF THE INVENTION

The present invention relates to a process for the isolation of natural thymol in crystalline form from *Monarda citriodora* (Jammu Monarda) oil. The process yields thymol crystals having 99% purity from crude thymol oil having more than 70% thymol, by gradually decreasing the temperature. In particular, the present invention involves crystallization of thymol at low temperature without involving any heating of the essential oil, while avoiding the use of harmful solvents like acetone, ethyl acetate, methanol and techniques like distillation or solid phase extraction. The invention is useful in multifarious industrial sectors, the majority being the healthcare sector; as thymol is an effective antiseptic, antibacterial and antifungal agent.

BACKGROUND OF THE INVENTION AND DESCRIPTION OF PRIOR ART

Thymol (THY) was first discovered by Neumann in 1719 and further purified by M. Lalleman in 1853. Different types of thymol sources have been mentioned in literature which can be further classified into natural and synthetic sources especially within highly found variety of Ajwain (*Trachspermum copticum*). Thyme containing THY oil in various *Thymus* species (*Thymus vulgaris, glandulosus, hemyalis, zygis, longicaulis, capitatus, riatarum, citriodorus, perscius, eriocalyx, daenensis* and *serpyllum* L), *Monarda* species (*Monarda punctata, didyma, fistulosa*), *Euphrasia rosstkoviana, Trachyspermum ammi* and *Origanum* species (*Origanum compactum, dicatamnus, vulgare*) have been reported. [Yakugaku Zasshi, 126: 1185-1190 (2006)] [J. Sci. Food Agric. 95: 2901-2907 (2015)].

Thymol has been used traditionally in India as well as China for various biological activities. Infact, thymol and its main natural source are employed for their positive potential in case of diverse therapeutic functions, namely, antioxidant, antimicrobial, anti-inflammatory, local anaesthetic, antiseptic, antibacterial, anthelmintic, spermicidal, depigmenting, analgesic, antidiarrhoeal, abortifacient, antihypertensive, insecticidal, anticholinesterase and antifungal activities. [RSC Adv. 4: 61975-61991 (2014)] [Food Chem. 210: 402-414 (2016)]. Generally, thymol is isolated from thyme herbs via fractional distillation [Int. J. Chem. Sci. 8: 729-743 (2010)] [J. Sci. Food Agric. 95: 2901-2907 (2015)] and it's also mentioned in the literature that aroma compounds degrade in the presence of high temperature. Therefore, there is always a demand by the pharmaceutical companies and flavor & fragrance association to get mass thymol. Also, isolation of thymol at cooling or without heating in order to isolate thymol (without any degradation) is always challenging.

Natural thymol products obtained by crystallization from crude natural oils can be used in foods, beverages, toothpaste, mouthwash etc. due to their preservative properties because of strong antimicrobial, antibacterial, antioxidant effects. The essential oils consist of about twenty four chemical compounds identified and quantitated by GC/MS, out of which thymol is the major chemical constituent.

Thymol (2-iso-propyl-5-methylphenol) is a naturally occurring monoterpene phenol which is isomeric with carvacrol and has shown antibacterial, antifungal, antitumor and anti-inflammatory activities. It also acts as an antioxidant, free radical scavenger and antilipid peroxidative agent.

Thymol acts as biocidal agent by causing disruption of the bacterial membrane. Due to its strong antiseptic, antioxidant properties, thymol has found applications as an herbal supplement to promote overall human health, as an additive in oral care compositions like mouthwashes to fight oral bacterial flora, as a food or beverage flavoring agent and also as a preservative due to its antimicrobial property. The therapeutic property of thymol is known since centuries, and a preparation from the thyme plant (thymol and carvacrol) was used by ancient Egyptians to preserve mummies. Thymol is an active ingredient of Listerine (mouthwash) and Vicks. In addition, it is a valuable intermediate in the production of synthetic menthol by catalytic hydrogenation. [Green Chem. 7: 288-293 (2005)] [Plant Cell Rep. 25: 993-996 (2006)].

*Monarda citriodora* Cerv. ex Lag. commonly known as Thymo-Herb belonging to family Lamiaceae, is an important aromatic herb and a natural source of essential oil. The species name comes from Latin for its "Citrus smell". It occurs on limestone glades, rocky prairies in Missouri and ranges from Texas and Mexico north to Missouri and Kansus. Therefore, the plant prefers light (sandy), medium (loamy) and heavy (clay) soils. It requires moist soil. The plant was introduced through seed to judge its performance in terms of essential oil quantity and its quality characteristics under sub-tropical environment. [BMC Microbiol. 17: 44-56 (2017)].

The leaves of the plant emit an aroma similar to that of lemon and therefore is commonly known as lemon mint or lemon beebalm. Due to a higher concentration of oils comprising various components such as thymol, carvacrol and geraniol in the leaves and buds of *Monarda* spp., the plant has been traditionally used to cure headache, fever, skin infections, minor wounds, stomach as well as bronchial ailments.

Essential oils comprising the said beneficial components like thymol, carvacrol, geraniol and other terpenes can be extracted from the plants using the known conventional methods such as steam distillation, hydro-distillation, solvent extraction and the like. The extracted essential oil can then be further processed to obtain the desired component in a purified state.

In short, it may be summarized that extraction of essential oils comprising thymol, thymoquinone, thymohydroquinone and carvacrol having anti-inflammatory properties against arthritis, cancer, viral infections and microbial infections from the leaves and seed heads of *Monarda fistulosa* and/or *Monarda didyma* plants using the conventional method of steam distillation is well known. However, the essential oil obtained from *Monarda* spp. can not only be used as a pharmaceutical composition, but can also be used as a food additive and as a flavoring agent.

The leaves of *Monarda citriodora* contain an abundant amount of thymol (62%), whereas the flowers of *M. citriodora* contain 51% thymol and the same can be extracted by supercritical extraction or by hexane extraction.

Other conventionally known methods of extracting essential oils from *Monarda* spp. or any other aromatic plant disclosed in the patents include vacuum distillation, electrophoresis, hydrodiffusion, nitrous oxide extractions and alcohol-based extractions.

A relatively newer method of extracting essential oils from plants disclosed in a patent is microwave-assisted extraction of essential oils. Microwave irradiations can be used to gradually increase the internal temperature of plant parts, such as leaves and flowers of *Monarda fistulosa* immersed in hexane in order to obtain volatile oil components such as geraniol, garlic oil, cedar oil, etc.

It is also reported that herbal extracts can be obtained from thyme, oregano, peppermint, spearmint, *Monarda* and marjoram by using food-grade solvents like hexane, heptane and/or acetone. A mixture of acetone and hexane can be used to extract the plant material such as the essential oil. The methods disclosed also include cooling down the mixture of solvent and plant material, followed by separating the solvent insoluble material and further processing to obtain the plant extract.

From the prior arts it can be inferred that carrying out oil extraction at higher temperatures generally favors an increase in oil yield. However, extraction at higher temperatures involve certain disadvantages like use of hazardous and flammable liquid organic solvents, antioxidant potential toxic emissions during extraction, costly and high purity solvents are required. The main disadvantage of extraction under reflux and steam distillation is that thermolabile components get degraded.

Therefore, keeping in view the drawbacks of the hitherto reported prior arts, the inventors of the present invention realized that there exists a dire need to provide a process of extracting crystallized thymol from *Monarda citriodora* by using an organic solvent like hexane as the extraction solvent and wherein gradually decreasing the temperature of the solvent (hexane): *Monarda* oil mixture, in a step wise manner yields highly pure crystals of thymol within 48 hours.

OBJECTIVES OF THE INVENTION

The main objective of the present invention is therefore to provide a process for the preparation of thymol crystals from crude thymol oil which obviates the drawbacks of the hitherto reported prior art.

Another object of the present invention is to provide a process wherein extraction is carried out using organic solvents at lower temperatures and wherein gradually decreasing the temperature of the reaction mixture yields highly pure crystals of thymol with 99 percent purity.

Still another object of the present invention is to provide a process wherein thymol crystals are formed directly from crude oil under controlled cooling of the crude thymol oil in a closed system.

Yet another object of the present invention is to provide a process for the preparation of thymol crystals which can be upscaled to produce pharmaceutical grade thymol.

SUMMARY OF THE INVENTION

The present invention relates to a process wherein crystallized thymol can be produced in 99% purity form especially in cool conditions from a new variety of *Monarda citriodora* (Jammu *Monarda*) crude oil with more than 70% recovery.

In the present invention, crystallized thymol has been obtained from a mixture of *Monarda* oil and a solvent like hexane in a 1:1 ratio. The process of recovering of thymol included gradually reducing the temperature of the hexane: *Monarda* oil mixture in a step-wise manner for obtaining highly pure crystals of thymol within 48 hours.

It is a primary aim of this invention to provide a thymol product by crystallization from natural crude *Monarda citriodora* (Jammu *Monarda*) oil which, can be incorporated into foods and beverages in trivial amounts due to strong antimicrobial, antibacterial, and antioxidant properties as well as used as a preservative. The crystallized thymol product purity was determined by gas chromatography/mass spectrometry (GCMS).

It is a further step of this invention to provide a method for obtaining a thymol product having the desired chemical and physical properties from the thymol rich crop *Monarda citriodora* (Jammu *Monarda*). The essential oil of *Monarda citriodora* (Jammu *Monarda*) consists of about twenty four chemical compounds identified and quantitated by GC/MS, out of which thymol was found to be the major chemical constituent.

It is a further aim of this invention to provide a method of obtaining a thymol product in maximum quantity with previously described properties wherein crystallization is carried out by different cooling temperature in the presence of solvent mixture.

Until now, various natural sources for thymol production have been reported but most of them are limited as well as costly because crude oil of related crops contains maximum 50% of thymol, whereas the *Monarda citriodora* (Jammu *Monarda*) variety contains 52 to 85% of thymol. In particular, existing crops for purifying thymol from crude thymol oil may require long process to isolate thymol from the crude thymol oil compositions. Furthermore, adaptation of previous source for thymol production processes to GMP regulation is likely to be costly because of the thymol percentage in handling thyme oil.

A new crop *Monarda citriodora* for the production of thymol has been developed that allows direct preparation of high purity thymol in maximum quantity from crude thymol oil. In the production process, thymol crystals are formed directly from crude oil under controlled cooling of the crude thymol oil in a closed system without the necessity of human contact with the crude Jammu *Monarda* oil. Thus, the methods disclosed herein can be easily adapted to GMP regulations, and may be used to produce pharmaceutical grade thymol.

In one embodiment, thymol crystals can be produced at cooling condition and further purified by simple filtration methods and no recrystallization or addition of additive to the crude oil is required to obtain highly pure thymol. The developed method takes significantly less time than previously reported thymol production methods. After purification, the thymol can be formed into pellets of suitable hardness and shape to prevent clumping and block formation of the solid thymol product even in the absence of additives. In some embodiments, the thymol production method is very simple and can readily be adapted to meet pharmaceutical Good Manufacturing Practices (GMP).

In most of the experiments, purity of isolated thymol varied from 95.5% to 99.5%.

The present embodiments involve methods for producing highly pure thymol through crystallization using gradual cooling under controlled temperature conditions. Using such a method, crystallization and purification of thymol may be completed in less than about one week, compared to prior thymol production methods. Thus, certain thymol production crop discussed herein may reduce the time for producing pure thymol crystals from about one or fewer weeks to about two to three days. Depending on the embodiment, production of highly pure thymol using the new developed crops and methods described herein may take about less than two weeks. Thus, the method can facilitate faster production of highly pure thymol. Furthermore, the decreased time requirements may increase the overall production of a particular pure thymol.

In an embodiment, the present invention provides a process for the isolation of thymol from naturally-occurring oils from *Monarda citriodora* (Jammu *Monarda*) involving the steps of lowering the temperature in order to achieve an adequate cooling ambience to get pure thymol.

In still another embodiment, the present invention provides a process for the isolation of thymol from naturally-occurring thymol oils from *Monarda citriodora* (Jammu *Monarda*) plant containing mixture of many compounds including thymol, p-cymene, gamma terpinene majorly and others like carvacrol, methyl carvacrol, alpha terpinene, beta-pinene, alpha-thujene in minute quantities using hexane in order to get pure crystals of thymol from Jammu *Monarda* oil in a ratio 50:50 (*Monarda* oil:hexane mixture).

In yet another embodiment, the present invention provides an isolation process claiming to minimize water in crude oil by keeping oil in cooling condition, separation of aqueous layer and dried over anhydrous salt such as sodium sulphate, magnesium sulphate etc. to remove water from the crude oil.

In still another embodiment, the present invention provides a process showing isolated recovery yield to be more than 70% without fractional distillation from *Monarda* oil:hexane mixture within 48 hours. In this invention, using hexane solvent in a particular ratio increased the crystallized thymol percentage in pure form.

In some embodiments, the particulates are cubic. The cubic/pellet form may be shaped, for example, using a pelletizer, from a thymol melt. Because the melting point of thymol is about 48° C., under cooled mixing conditions, the thymol is changed to a solid state and can further form a desired shape.

In a preferred embodiment, the present invention provides a process for the preparation of natural crystallized thymol from *Monarda citriodora* (Jammu *Monarda*) oil, wherein the steps comprising:

[a] filtering the crude Jammu *Monarda* oil followed by refrigeration at temperature ranging from 0 to 8° C. for 6 to 48 hours;

[b] separating the organic layer from the aqueous layer in the refrigerated oil of step and optionally drying the aqueous layer over an anhydrous salt;

[c] adding hexane to the organic layer obtained in step [b] followed by refrigeration at a temperature ranging ranging from 0 to 8° C. for 6 to 48 hours;

[d] filtering the refrigerated mix of step [c] to separate the thymol crystals from the dethymolised oil.

In another preferred embodiment, the present invention provides a process wherein the ratio of hexane to the organic layer is 1:1.

In still another preferred embodiment, the present invention provides a process wherein refrigeration is done at 0° C. for 48 hours.

In yet another preferred embodiment, the present invention provides a process wherein the yield of thymol is in the range of 13 to 71% with 99% purity.

In still another preferred embodiment, the present invention provides a process wherein the anhydrous salt is selected from sodium sulphate and magnesium sulphate.

DEFINITIONS

As used herein, "crude thymol oil" refers to oils distilled from a *Monarda citriodora* (Jammu *Monarda*) plant (belonging to family Lamiaceae), whose oils contain at least 52-85% thymol calculated by GCMS experiment.

As used herein, "dethymolised oil (DTO)" refers to components of crude thymol oil remaining after at least partially removing thymol from the oil.

DETAILED DESCRIPTION OF THE INVENTION

The plant Jammu *Monarda* (*Monarda citriodora*) used for the purposes of the present invention was cultivated at the experimental farm of CSIR-IIIM Chatha, J&K-180009, India which is situated just 11 km far away from Jammu city. The seeds of the crop was sown in the nursery beds in the month of first fortnight of October, 2016 and transplanted the seedling in the field of CSIR-IIIM experimental farm, Chatha in the month of November, 2016. The crop was allowed to grow up to month of April, 2016. Periodic sampling for the essential oil was done during the crop growth season with the help of Clevenger apparatus and accordingly these essential Oil samples were analyzed. For Large scale experiments, the oil was extracted at the experimental field, Chatha with the help of hydro steam distillation unit in 3 hours and 30 minutes. Oil recovery from this crop falls between the ranges from 0.4% to 0.5% depends on the management and time of harvesting of the crop.

The thymol production methods disclosed herein can be used for direct production of highly pure thymol from crude *Monarda citriodora* (Jammu *Monarda*) oil. For example, methods disclosed herein can be used to produce pharmaceutical grade thymol. Production of thymol according to various methods disclosed herein may take one week or less. However, in some embodiments, the thymol was obtained within 48 h. In the present invention, the temperature of *Monarda* oil:hexane mixture (1:1 ratio) has been gradually decreased to yield pure crystals of thymol. Also, the process provides the desired recovery yield of more than 70% thymol from *Monarda* oil:hexane mixture within 48 hours.

Figure 1:
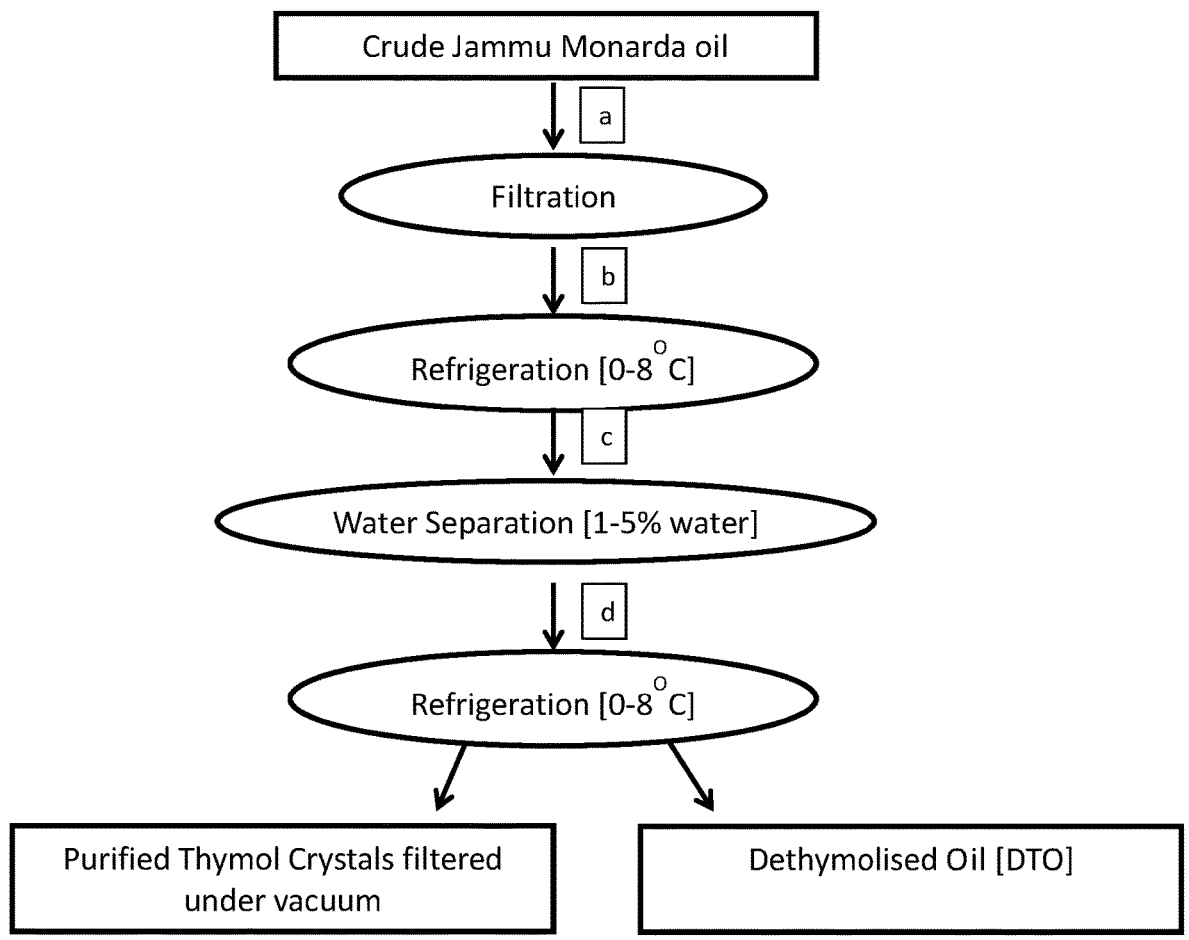
FIG. 1 Flow chart diagram showing steps for purifying thymol
Figure 2:
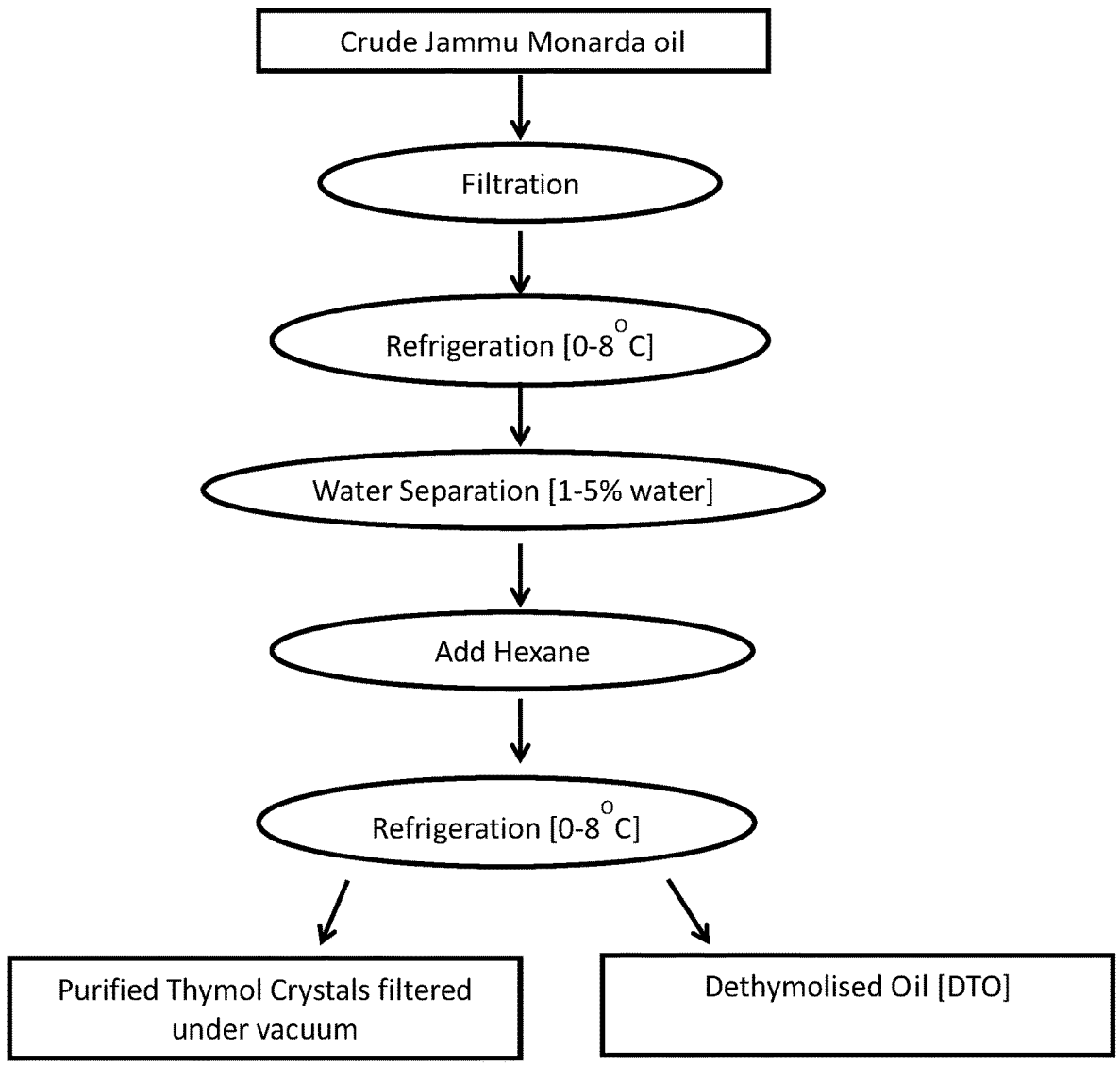
FIG. 2 Flow chart diagram showing steps for purifying thymol by using Hexane
Figure 3:
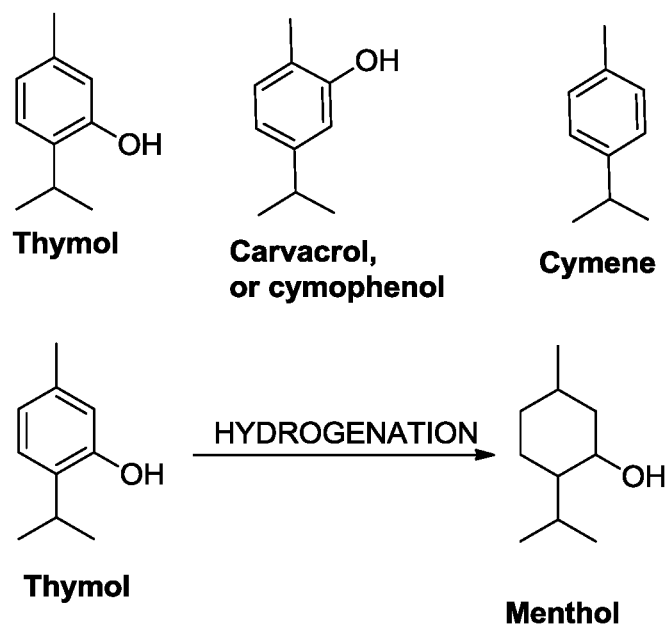
FIG. 3 Structure of thymol and its various analogues

In FIGS. 1 and 2, an exemplary method for thymol production is illustrated. Depending on the embodiment, the method of may include fewer or additional blocks and/to the blocks may be performed in a different order than is illustrated.

Crude thymol oil is provided at block 1. The source and type of the crude thymol oil is *Monarda citriodora* (Jammu *Monarda*). In some embodiments, the crude thymol oil contains 1 to 5% water due to crude thymol oil prepared by steam distillation from *Monarda citriodora* plant material.

The concentration of thymol in the crude *Monarda citriodora* (Jammu *Monarda*) oil is not permanent; it remains approximately 52% to 85% thymol by assessed by GCMS analysis and varies according to climate and storage conditions.

The crude thymol oil, in some embodiments, includes few, if any, added organic solvents. By avoiding the use of significant amounts of organic solvent, the methods disclosed herein may not require additional steps of removing organic solvents. Furthermore, the methods disclosed herein may be more economical compared to other methods requiring costly organic solvents. In some embodiments, the crude thymol oil is substantially free of an organic solvent (e.g., not more than trace amounts).

FIGS. 1 and 2 represent purification steps for crude *Monarda citriodora* (Jammu *Monarda*) oil performed within the laboratory. Before crystallizing the thymol, seed crystals of thymol may optionally be introduced to aid crystallization. Adding seed crystals of thymol may improve the rate of crystallization.

Seed crystals of thymol may also be introduced, in some embodiments, by rapidly cooling a portion of the crude oil to form seed crystals of thymol. In some embodiments, seed crystals are formed by exposing a portion of the crude *Monarda citriodora* oil to one or more cooling surfaces having a temperature of not more than about 10° C. For example, experiments were done with various cooling temperature, wherein for instance, the refrigerator having temperature ranging from 0 to 8° C. can be used for making seed crystals.

In some embodiments, after the seed crystals have been formed, the temperature of the one or more cooling surfaces is adjusted to a crystallization starting temperature between 0-8° C. In some embodiments, seed crystals are not introduced, and crystallization occurs at 0-8° C. within 48-72 h without introducing seed crystals of thymol.

The crude thymol oil is crystallized according to FIG. 1 to purify the material. As an example, the crude *Monarda citriodora* (Jammu *Monarda*) oil is kept in refrigerator for separation of water layer which is soluble in oil (1-5% water), separated by separating funnel after which the crude oil is dried by anhydrous salt (such as anhydrous sodium sulphate, magnesium sulphate etc.) followed by filtering off the oil, storing in a flask and gradually cooling to obtain crystalline thymol. Yield of obtained crystalline thymol varies according to the cooling temperature (refer Table 1) especially in the absence of seed crystals (preferably a cooling temperature in the range of about 0° C. to 10° C. (because the melting point of thymol crystals is about 48 to 51° C. and boiling point 232° C.). In general, thymol crystal formation may occur over a period of about 48 h.

TABLE 1

Effect of Different temperatures on the preparation of thymol crystals

| Exp. No. | Quantity | Temp. (° C.) | Time (h) | Yield (%) | Observations |
|---|---|---|---|---|---|
| 1 | 1 L | 8-10 | 48 | — | No crystal formation was observed till 48 h |
| 2 | 1 L | 6 | 48 | 13% | Crystal formation was observed after 6 h, and isolated with 95% purity after 48 h. |
| 3 | 1 L | 4 | 48 | 38% | Crystals were isolated with 99% purity |
| 4. | 1 L | 0 | 48 | 63% | Crystals were isolated as white powder with 98-99% purity |
| 5. | 1 L | 0 | 48 | 73% | Improvement in yield was observed while addition of Hexane in Oil (1:1) ratio |
| 6 | 1 L | Base/Acid treatment (20% NaOH) | 48 | 59% | Brownish color crystals were isolated with 90% purity. |

Also The effect of different time duration was observed on thymol crystal formation and 48 h was set as the standardized time.

TABLE 2 depicts the results of thymol crystal formation when different ratios of hexane to organic layer are used.

| Sl No. | Volume of hexane | Volume of organic layer | Crystal formation (Yield in %)/remarks |
|---|---|---|---|
| 1. | 250 mL | 1 L | 63% |
| 2. | 500 mL | 1 L | 65% |
| 3. | 1 L | 1 L | 72% |
| 4. | 1.5 L | 1 L | 70% |

Note:
Slightly decrease in yield was observed when volume of hexane increase from 1 L to 1.5 L.

The initial crystallization temperature (at the start time of the crystallization process, may be a temperature at which the thymol is a liquid. Depending on the embodiment, the initial crystallization temperature was observed to be ranging from 8 to 10° C. (Table 1, experiment 1), In general, during gradual cooling for crystallization of thymol, the crystallization chamber is initially cooled at 0-10° C. for initial 48 hours. The rate of cooling may be determined based on several factors. For example, the concentration of thymol in the crude Jammu *Monarda* oil may be used in determining the rate of cooling.

In another embodiment, the crude *Monarda citriodora* (Jammu *Monarda*) oil after treating as per the process according to FIG. 2, was kept for 48 h at 8 to 10° C., but no crystal formation was found within 48 h at this temperature (Table 1).

In still another embodiment, the cooling temperature was set at 6° C. and crystal formation was observed after 24 h overall 13% pure thymol crystal was obtained within 48 h, Yield may vary in response to time at this set temp.

In yet another embodiment, the initial cooling temperature was set at 4° C. and 0° C. respectively. Yield of thymol increased by decreasing the temperature within 48 hours (Table 1).

In another embodiment, the ratio of organic layer and added hexane is in the range of 1:0.25 to 1:1.5.

In still another embodiment, after treatment of *Monarda citriodora* (Jammu *Monarda*) according to FIG. 2, organic layer and added hexane is in a ratio of 1:1, and the initial crystallization temperature was set to 0° C., for 48 h. The obtained yield of thymol was observed to be more than 70%. In this example, using the hexane solvent in a particular ratio increased the crystallized thymol percentage. As described in Table 1, percentage of obtained pure thymol may vary according to cooling periods (more or less than 48 h).

After crystallization, the thymol crystals may optionally be further dried by filtration assembly with a subsequent vacuum. Purity of obtained thymol was monitored by GCMS. In the purification process (during filtration by using vacuum), solid crystal formation was also observed in filtration flask, whereby the vacuum helped in decreasing temperature; which can be a reason to observe the crystals.

The dethymolised oil (DTO) that remains after the crystallization process is stored in different container (because of presence of important molecule such as cervical, cymene etc.). As described above, the dethymolised oil includes the remaining liquid after crystallizing the thymol in the crude *Monarda citriodora* (Jammu *Monarda*) oil (e. g., after the crystallization described in FIG. 2)

In some embodiments, cooled water or cooled hexane is passed over the thymol crystals to remove the dethymolised oil from the crystals. Accordingly, passing a cooled solvent over the thymol crystals can improve the purity of the crystals and expedite removing dethymolised oil.

After obtaining purified thymol, it can be transferred to a stock tank. Generally, for transferring the thymol as liquid, the crystallized thymol can be warmed to about 50-60° C. to melt the thymol crystals. The melted thymol can then be transferred to, for example, a stock tank.

In some embodiments, the purified thymol can be formed into particulate for ease of handling. In some embodiments, solid, purified thymol is comminuted (e.g., grinding, milling, cutting, etc.) into particulate. In some embodiments, the particulate are cubic. The cubic/pellet form may be shaped, for example, using a pelletizer, from a thymol melt. Because the melting point of thymol is about 48° C., under cooled mixing conditions, the thymol is changed to a solid state and can further form a desired shape.

The purified thymol can be loaded into the cooling tray mixer that is maintained at a temperature below 10° C. The thymol pellets can be packaged into packing containers for shipping or storage.

Production of *Monarda citriodora* (Jammu *Monarda*) Oil

*Monarda citriodora* crop was cultivated at field CSIR-IIIM, research station Chatha in the year of 2016-17. The crop was transplanted after proper preparation of the land with proper layout and proper crop geometry. All agricultural inputs i.e.; weeding, hoeing, irrigation, fertilizer applications were provided according to the package of practices. The crop was monitored time to time and managed scientifically. It was allowed to mature up to harvesting. Maturity was governed with the help of data recorded for essential oil recovery and quality with the help of Clevenger apparatus. Quality was governed with the help of GCMS. Essential Oil recovery was obtained with the help of periodic samples distilled with Clevenger apparatus. The fresh herbage of *Monarda citriodora* (5178 kg) was distilled by using hydro steam distillation unit with direct fire system. Essential oil was recovered=20.52 liters. The Essential Oil recovery was 0.40%.

1 L Jammu *Monarda* oil=760 g

Percentage of thymol in Procured Jammu *Monarda* oil=52%

Note: The concentration of thymol in the crude *Monarda citriodora* (Jammu *Monarda*) oil is not permanent; it ranges approximately from 52% to 85% thymol by GCMS analysis and varies according to climate and storage condition.

Thereby, 1 L or 760 g Jammu *Monarda* oil=395 g (yield 100%) thymol

Isolation of thymol/Isolated thymol $$\text{crystals}(\%\ \text{yield}) = \frac{\text{Actual yield}}{\text{Theoretical yield (395 g)}} \times 100$$

EXAMPLES

The following examples are given by way of illustration only and therefore should not be construed to limit the scope of the present invention in any manner.

Example 1

Crude oil of *Monarda citriodora* (Jammu *Monarda*) that contain 52% thymol oil was transferred in 1 Liter glass bottle through a funnel. The crude oil was cooled in the refrigerator for 10-12 hours. After cooling of the oil two layers were formed in the bottle, an organic layer and an aqueous layer (1 to 5% water). The separated oil was stored in a glass bottle and kept in the refrigerator at 8-10° C. for crystallization (table 1). At the end of 48 hours, no crystal formation occurred in the thymol oil.

Example 2

This method illustrates the effect of temperature on crystallization of thymol. Crude oil of *Monarda citriodora* having 52% thymol was transferred in 1 liter glass bottle and kept in a refrigerator for 10-12 hours. Two layers were formed in the bottle, an organic layer and an aqueous layer. The aqueous layer was separated with the help of separating funnel and the organic layer (oil) was stored in the glass bottle. The bottle was kept in the refrigerator for crystallization and at the end of 48 hours no crystallization was observed. The oil was taken in 1 liter glass bottle and kept in a refrigerator at 6° C. temperature for 48 hours. It was observed that crystallization was initiated after 6 hours in the oil. Dethymolised oil (DTO) was removed from thymol crystals with the help of Buchner funnel and vacuum pump. By this method 50 g (Yield 12.65%) thymol crystal was isolated. The purity of these crystals was monitored by GCMS analysis which was found to be 95.5%.

Example 3

For thymol oil separation from crude oil of *Monarda citriodora* (52% thymol oil) 1 liter oil was transferred into a glass bottle through a funnel and kept in the refrigerator for cooling. After that, layer formation occurred comprising an organic layer and an aqueous layer. Aqueous layer was separated from the oil and oil was dried over anhydrous salt. Further oil was filtered and transferred to a glass bottle, kept in the refrigerator at 4° C. for 48 hours. At the end of 48 hours, crystal formation was observed in the oil. DTO was separated from thymol crystals using Buchner funnel as well as a vacuum pump and further stored in a bottle. 150 g (Yield 37.97%) thymol crystals were isolated and on GCMS, 99% purity was observed. Therefore, high yield of thymol crystals was obtained by decreasing temperature.

Example 4

Crude oil of *Monarda citriodora* (52% thymol oil) was transferred in to 1 liter glass bottle through a funnel and kept in a refrigerator for cooling. Due to cooling, layer formation occurred in oil, an organic layer and an aqueous layer. Aqueous layer was separated from oil using separating funnel and anhydrous salt added in the organic layer (oil) for drying. Further, oil was filtered and transferred to a glass bottle, kept in the refrigerator at 0° C. for 48 hours and crystals were observed in the bottle. The crystals were separated from dethymolised oil. From this method, 250 g (yield 63.29% yield) pure white crystals were isolated with 98% purity (according to GCMS analysis). It was observed that in this method at 0° C. an elevated yield of thymol crystals was obtained.

Example 5

Crude oil of *Monarda citriodora* having 52% thymol was transferred in 1 liter glass bottle and kept in a refrigerator for 10-12 hours. After that two layers were formed in the bottle; an organic layer and an aqueous layer. The aqueous layer was separated with the help of separating funnel and the organic layer (oil) stored in a glass bottle. Then thymol oil with hexane was taken in a glass bottle (1 liter thymol oil and 1 liter hexane), in a ratio of 1:1). The bottle was kept in the refrigerator for crystallization at 0° C. for 48 h. After the stipulated time, crystal formation was noticed in the bottle and later oil was separated from crystals through Buchner funnel and vacuum pump. 285 g (Yield 72.15%) pure thymol crystals were isolated with 95.5% purity.

Example 6

Thymol oil was taken in a glass bottle, first treated with aqueous 20% NaOH solution (500 mL) and kept in a refrigerator for one day. The aqueous layer (Containing thymol salt) and organic layer were separated by separating funnel. The aqueous layer was then transferred to a glass bottle and treated with 20% HCl/water solution (1 L) and stored in a refrigerator again for one day. After one day, brown colored thymol crystals were observed in the water layer and filtered through vacuum pump and Buchner funnel. From this method, 230 g (Yield 58.22%) thymol crystal were observed.

Advantages of the Invention the developed process allows direct preparation of high purity thymol (approx. 99%) in maximum quantity from crude thymol oil.
In the production process, thymol crystals are formed directly from crude oil under controlled cooling of the crude thymol oil in a closed system without the necessity of human contact with the crude Jammu *Monarda* oil.
The methods disclosed herein can be easily adapted to GMP regulations, and may be used to produce pharmaceutical grade thymol.

The invention claimed is:

1. A process for the preparation of natural crystallized thymol from *Monarda citriodora* (Jammu Monarda) oil, wherein the steps comprising:
   [a] filtering the crude Jammu Monarda oil followed by refrigeration at temperature ranging from 0 to 8° C. for 6 to 48 hours;
   [b] separating the organic layer from the aqueous layer in the refrigerated oil of step and optionally drying the aqueous layer over an anhydrous salt;
   [c] adding hexane to the organic layer obtained in step [b] followed by refrigeration at a temperature ranging ranging from 0 to 8° C. for 6 to 48 hours;
   [d] filtering the refrigerated mix of step [c] to separate the thymol crystals from the dethymolised oil.

2. The process as claimed in claim 1, wherein the ratio of hexane to the organic layer is 1:1.

3. The process as claimed in claim 1, wherein refrigeration in step [c] is done at 0° C. for 48 hours.

4. The process as claimed in claim 1, wherein the yield of thymol is in the range of 13 to 71% with 99% purity.

5. The process as claimed in claim 1, wherein the anhydrous salt is selected from sodium sulphate and magnesium sulphate.

\* \* \* \* \*